United States Patent [19]
Hudson et al.

[11] Patent Number: 5,147,608
[45] Date of Patent: Sep. 15, 1992

[54] APPARATUS AND PROCESS FOR PERFORMING REPETITIVE CHEMICAL PROCESSING

[75] Inventors: Derek Hudson, San Anselmo; Jordan Honig, San Francisco; Ronald M. Cook, Ross; Douglas J. Ng, El Cerrito, all of Calif.

[73] Assignee: Millipore Corporation, Bedford, Mass.

[21] Appl. No.: 188,453

[22] Filed: Apr. 29, 1988

[51] Int. Cl.⁵ .......................................... G01N 33/68
[52] U.S. Cl. ..................................... 422/63; 422/105; 436/43; 436/89; 525/54.11; 530/333; 530/334; 935/88
[58] Field of Search ............... 422/62, 105, 130, 63; 525/54.11; 935/88; 436/89, 43; 530/333, 334

[56] References Cited

U.S. PATENT DOCUMENTS

| | | | |
|---|---|---|---|
| 3,531,258 | 9/1970 | Merrifield et al. | 23/252 |
| 3,557,077 | 1/1971 | Brunfeldt et al. | 260/112.5 |
| 3,645,689 | 2/1972 | Sjoquist | 23/230 |
| 3,647,390 | 3/1972 | Kubodera et al. | 23/252 |
| 3,715,190 | 2/1973 | Won Kil Park et al. | 23/252 |
| 3,717,436 | 2/1973 | Penhasi et al. | 23/230 |
| 3,856,471 | 12/1974 | Winitz et al. | 23/253 |
| 3,892,531 | 7/1975 | Gilbert | 23/253 |
| 3,959,307 | 5/1976 | Wittmann nee Liebold et al. | 260/309.5 |
| 4,065,412 | 12/1977 | Dreyer | 260/8 |
| 4,108,846 | 8/1978 | Meienhofer | 260/112.5 |
| 4,362,699 | 12/1982 | Verlander et al. | 422/131 |
| 4,483,964 | 11/1984 | Urdea et al. | 525/54.11 |
| 4,517,338 | 5/1985 | Urdea et al. | 525/54.11 |
| 4,598,049 | 7/1986 | Zelinka et al. | 435/287 |
| 4,665,037 | 5/1987 | Stolwitz | 436/89 |
| 4,668,476 | 5/1987 | Bridgham et al. | 422/62 |
| 4,671,941 | 6/1987 | Niina et al. | 422/131 |
| 4,701,304 | 10/1987 | Horn et al. | 422/62 |

FOREIGN PATENT DOCUMENTS 58-194896 11/1983 Japan ..................................... 935/88

Primary Examiner—Robert J. Warden
Assistant Examiner—Timothy M. McMahon
Attorney, Agent, or Firm—Hamilton, Brooks, Smith & Reynolds

[57] ABSTRACT

A chemical processing system is disclosed for the automated dissolution, dispersing and reaction of chemicals, especially for synthesizing proteins. The system includes a plurality of storage cartridges containing a first chemical in fluid communication with a reservoir containing a second chemical to be reacted with the first chemical. Each cartridge includes a pump (e.g., a plunger) which operates by changing the internal volume of the cartridge. The pump permits bi-directional flow of the first chemical into and out of the reservoir and cartridge to promote mixing and reacting with the second chemical in the reservoir to produce a third chemical.

13 Claims, 5 Drawing Sheets

APPARATUS AND PROCESS FOR PERFORMING REPETITIVE CHEMICAL PROCESSING

FIELD OF THE INVENTION

This invention relates to systems and procedures for chemical analysis, sequencing operations and synthesis. More particularly, the invention relates to an apparatus and process for the automated synthesizing of proteins, especially peptides.

BACKGROUND OF THE INVENTION

The accurate dissolution, dispensing and reaction of chemicals has numerous applications. These include analytical procedures such as, for example, the derivitization for HPLC determination of amino acid composition; sequencing operations such as in the Edman degradation procedure; and in synthesis of various substances, such as RNA, DNA, peptide and oligosaccharide assemblies.

Moreover, a growing number of research facilities, especially non-chemical laboratories, require synthetic peptides. In conventional practice, the production of synthetic peptides requires the work of chemists who are highly skilled in synthetic chemistry. This, and the necessity of exercising precise control of the chemicals to be added in a process, including quantity, sequence, timing, and the like, adds to the cost and time required to produce a given result, and may lead to inaccuracies.

Patents of interest which are exemplary of the state-of-the-art in this field are Verlander et al U.S. Pat. No. 4,362,699, issued Dec. 7, 1982, entitled "APPARATUS FOR HIGH PRESSURE PEPTIDE SYNTHESIS" and Bridgham et al U.S. Pat. No. 4,668,476, issued May 26, 1987, entitled "AUTOMATED POLYPEPTIDE SYNTHESIS APPARATUS", the disclosures of which are incorporated herein by reference in their entirety.

SUMMARY OF THE INVENTION

Accordingly, it is an object of this invention to provide a simple and inexpensive automated system for the dissolution, dispensing and reaction of chemicals, especially for the synthesizing of peptides.

Another object of the invention is to provide a peptide synthesizer in which simplicity and low cost are achieved by utilizing fixed chemical protocols, prepackaged Fmoc chemistry and a synthesis-dedicated computer.

A further object of the invention is to provide a novel apparatus and method for the storage and delivery of amino acids in the synthesizing of peptides and proteins.

Yet another object of the invention is to provide a system for the automated control of analytical procedures, sequencing operations and synthesis of chemicals.

Another object of the invention is to provide a novel means for the storage, dissolution and dispensing of a chemical, and its subsequent use as a pump in a reaction process involving the chemical.

An even further object of the invention is to provide a means for sequentially advancing containers of a chemical to a work station.

Still another object of the invention is to provide a unique, reusable reaction vessel having means permitting replacement of solid supports in the vessel.

The foregoing and other objects and advantages of the invention are achieved with an automated system including a synthesis apparatus and a computer-operated control. The apparatus includes a novel fluid transport system that incorporates a syringe-type amino acid dissolution and delivery system with a flow-through reusable reactor. The computer control utilizes a pull-down menu and requires a minimum of keystrokes, thus making possible operation by most, if not all, laboratory personnel.

For synthesis of peptides, the invention makes particular use of the fact that mixtures of solid Fmoc-protected amino acids and BOP (benzotriazolyloxytris-(dimethylamino)phosphonium hexafluorophosphate, optionally with equimolar amount of HOBt (hydroxybenzotriazole), are stable when stored under dry conditions. When these are dissolved in activator (N-methylmorpholine in DMF), rapid formation of a highly active (greater than symmetric anhydrides) and long lasting intermediate occurs. The chemistry protocol follows the basic Fmoc deblock-couple cycle, but the long lived intermediate allows the coupling time for difficult sequences to be extended rather than resorting to the "double coupling" schemes used in the prior art.

The mixtures of amino acid, BOP and HOBt are provided in disposable syringe-type cartridges. The cartridges are loaded in a rotating carousel for sequential access under control of the automated system. The solid supports are loaded into the reusable reaction vessel, and prepared reagent solutions are stored and dispensed from a plurality of reservoirs contained within the apparatus. Bulk solvents and waste solutions are contained in suitable external reservoirs.

After entering a desired sequence at the computer work station with appropriately written software programs, the user can choose to have the apparatus calculate reagent requirements for the synthesis. These calculations can then be used as a guide in loading the reagents in the synthesizer.

The cartridge in which the amino acid powder is stored functions not only to preferably store the amino acid in a dry, hermetically sealed environment, but after connection to the fluid transport system, also functions as a syringe pump to draw solvents and reagents into the cartridge for dissolution and reaction of the contents when the syringe plunger is raised, and for then expelling the dissolved and reacted materials to a further reactor or reactors or analysis unit or units by depressing the plunger of the syringe. Following initial dispensation, the solution may be drawn back into the cartridge for subsequent delivery to further reactors or analysis units. In a particular application, e.g., peptide synthesis, the reaction solution can advantageously be reciprocated backwards and forwards between the reactor(s) and the cartridge, providing suspension and re-suspension of the synthesis support material(s), thereby assuring uniform and near quantitative reaction. The reciprocation further aids in dissolution of poorly soluble materials.

After dissolution and dispensation of its contents, the cartridge serves as a syringe pump for the metering, dispensation and mixing of other reagents and solvents accessible from the fluid system. Because of their accuracy and variable dispensation rates, syringe pumps are attractive for administering fluid dispensation in synthesis, sequencing and analytical instrumentation. However, they have not been widely used because of reliability problems. The disposable syringe of the present invention solves this problem since it can be, and preferably is, discarded after each cycle of operation.

The carousel in which the cartridges are carried and supported for sequential access has a plurality of radial slots in its periphery for receiving the cartridges and includes a clamping structure for securely clamping the cartridges in place. The carousel is indexed through predetermined arcs of movement to bring the cartridges into operative position for dissolution, reaction and dispensation of the contents of the cartridges. Indexing of the carousel is controlled by a motor operated in response to strategically placed sensors and the computer control system.

A plunger gripping and actuating device is positioned above the carousel in position to intercept and engage a flange on the cartridge plunger as the carousel is indexed, and thereafter to move the plunger up and down to draw a solvent and/or reagent into the cartridge to dissolve and dispense the contents into the fluid system for reaction with selected reagents contained in suitable reservoirs. Under control of the computer system, the plunger gripping and actuating device reciprocates the plunger to cause the cartridge and plunger to function as a syringe pump for mixing, etc., of the contents of the cartridge with other reagents, etc, contained in the fluid system.

The fluid system includes a plurality of valves which are operated in a predetermined sequence to introduce different materials, and/or to cause flow of the material(s) to and from different parts of the system.

A novel reactor column for containing the solid supports used in peptide synthesis, for example, has a snap-together body for access to the solid supports.

BRIEF DESCRIPTION OF THE DRAWINGS

The foregoing and other objects and advantages of the invention will become apparent from the following detailed description when considered with the accompanying drawings, wherein like reference characters designate like parts throughout the several views, and wherein.

DETAILED DESCRIPTION OF THE PREFERRED EMBODIMENTS

Figure 1:
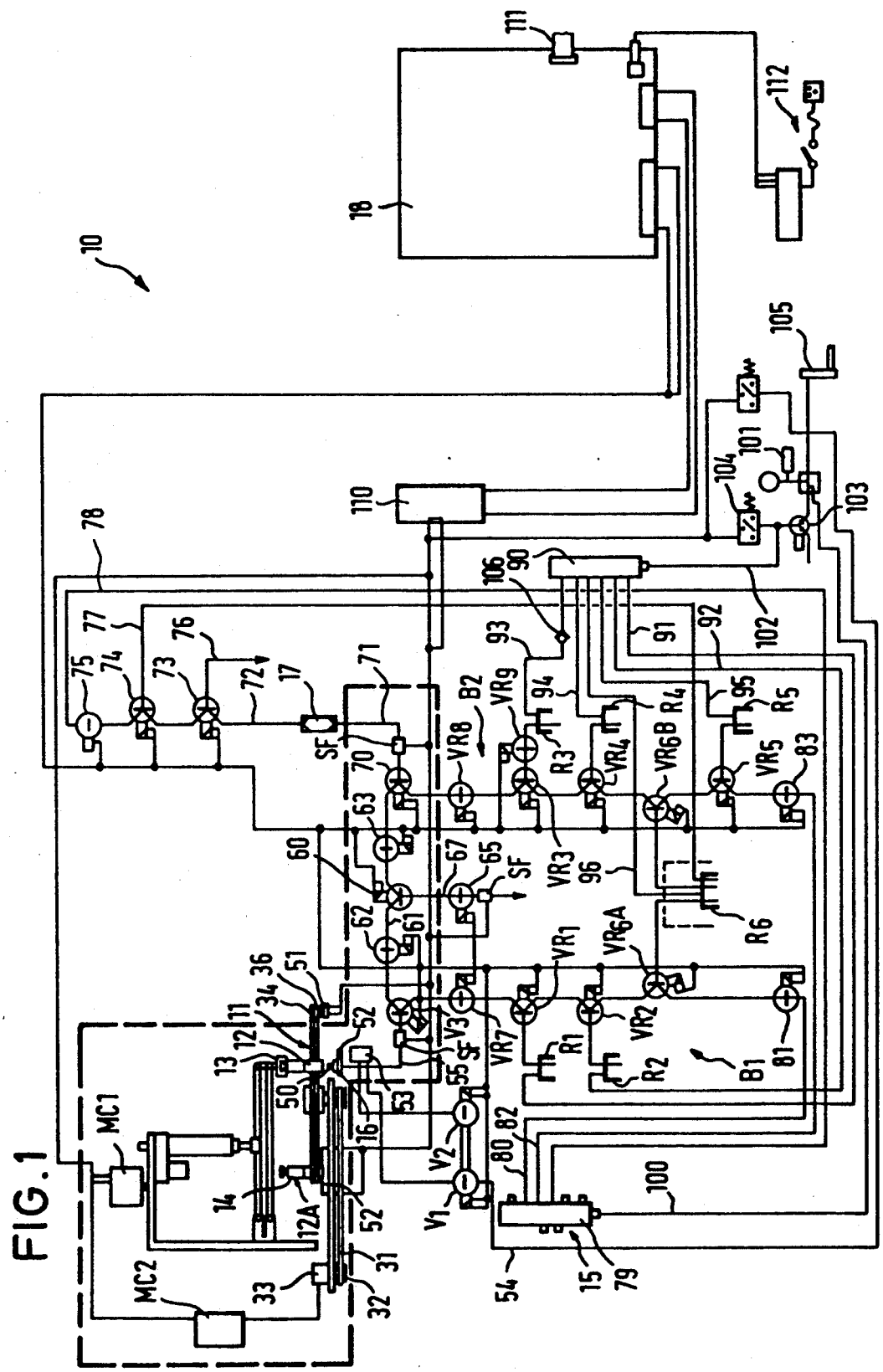
FIG. 1 is a schematic diagram of the system used in the invention.

With more particular reference to the drawings, the system of the invention is indicated generally at 10 in FIG. 1. As defined hereinafter, the system is intended for synthesis of peptides, but, as noted earlier, it could also be used for other processes. The system includes a carousel 11 in which the cartridges 12 are supported; a linearly actuated gripper mechanism 13 for gripping and reciprocating the plunger 14 of a cartridge; a fluid transport system 15, including a fluid connector 16 and reactor column 17; and an electronic control including board 18.

Figure 2:
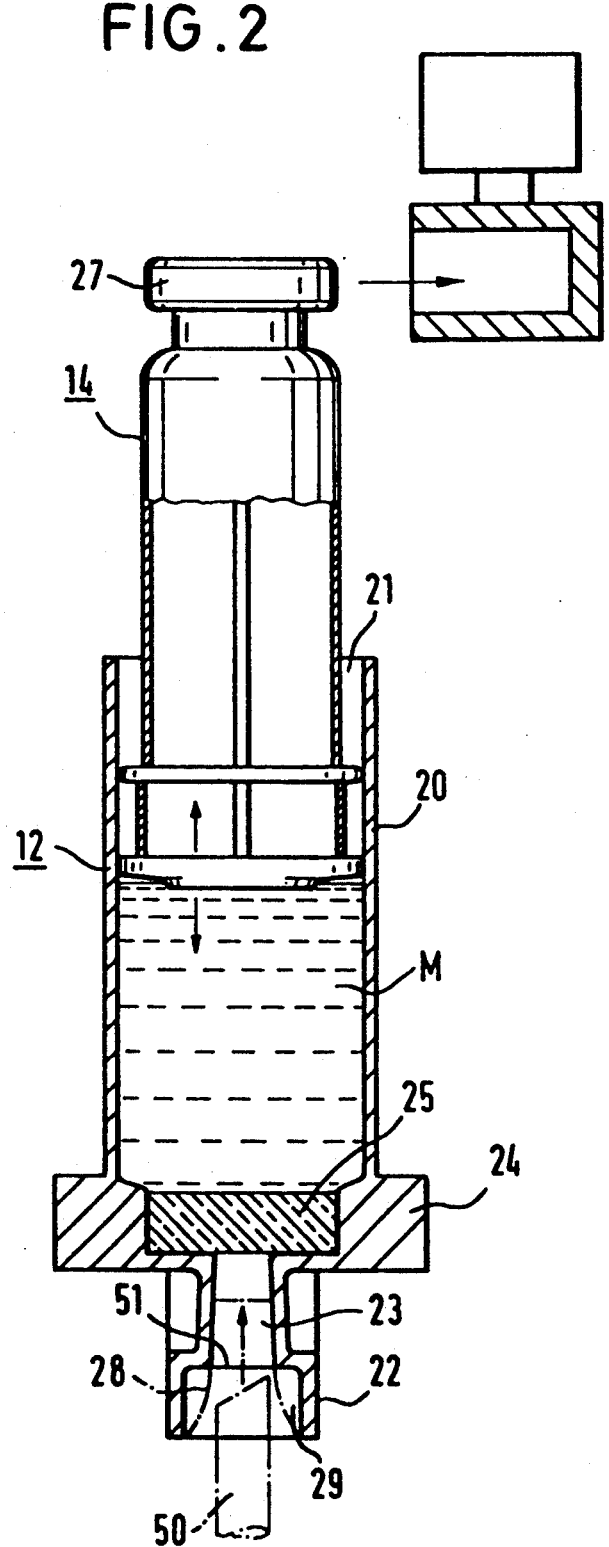
FIG. 2 is an enlarged, longitudinal sectional view of the unique cartridge used in the system of the invention.
Figure 3:
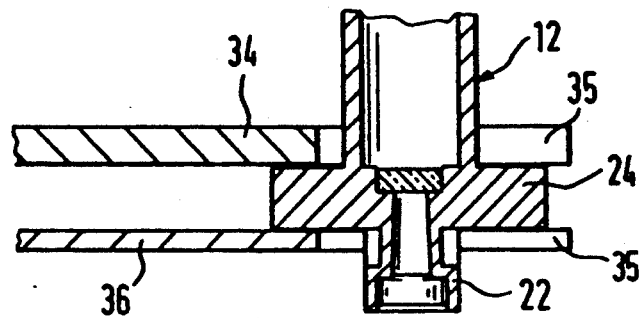
FIG. 3 is an enlarged, fragmentary sectional view of a portion of the cartridge and carousel, showing the manner in which the cartridge is gripped and held by the plates of the carousel.
Figure 4:
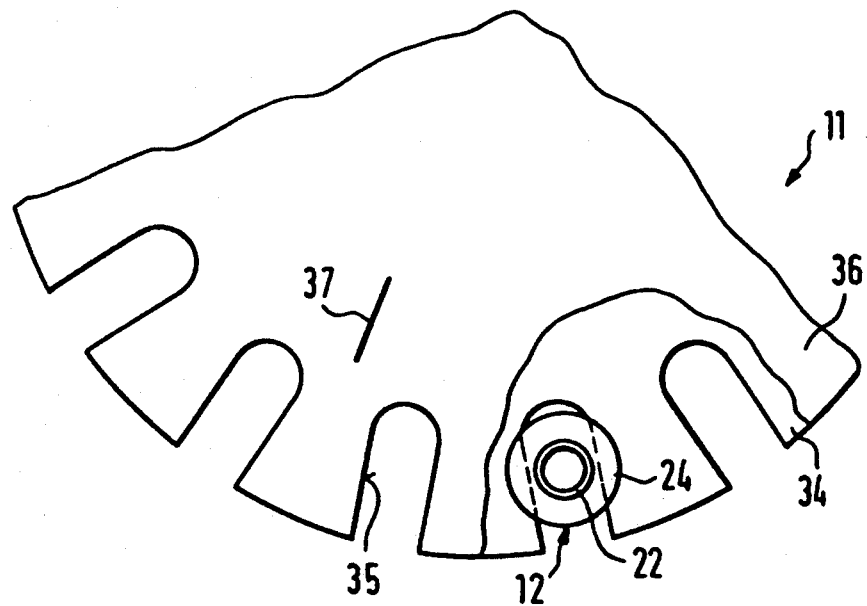
FIG. 4 is bottom plan view of the carousel, with a portion thereof broken away, showing the slotted configuration and the relationship of the flange on the cartridge to the slotted carousel plates.
Figure 5:
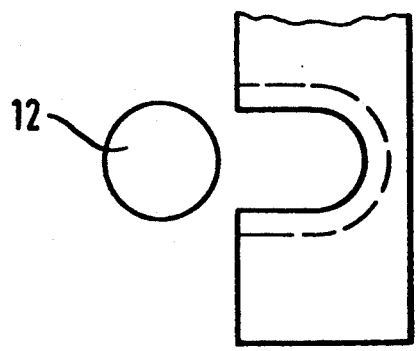
FIG. 5 is an enlarged, fragmentary top view of a portion of the plunger gripper, showing its relationship to a cartridge as the cartridge advances toward operative relationship with the gripper.

The syringe-type cartridge 12 comprises a modified disposable syringe designed for automation. The cartridge is initially used for storage of the solid amino acid mixtures "M", and includes an elongate cylindrical body 20 having an open upper end 21 and a reduced diameter lower end 22 having a tapered bore 23 therein defining a friction fit female connection. The cartridge volume should preferably be about 5 ml. A diametrically enlarged gripping flange 24 is formed on the outside of the body near the lower end thereof. As seen best in FIG. 2, a foraminous block or frit 25 is secured within the body in the area of the flange 24 and defines a mechanical barrier against leakage of the solid reagents. The frit preferably has a filtration ability of about 125 microns for the materials described herein.

The plunger 14 is slidably sealed in the cylindrical housing or body, whereby the solid amino acid mixture "M" is confined within the cartridge body between the frit 25 and the plunger 14. The plunger has an enlarged flange 27 on its outer, free end, for a purpose to be later described, and as assembled and ready for use, is positioned about one-half the distance into the cartridge. Pumping action of the plunger in the cartridge is capable of drawing 2.5 ml of DMF (dimethyl formamide) and amino acid back through the reaction column 17 as well as pushing it forward through the column and is capable of moving a volume of 5 ml in either direction during a full stroke.

A hermetic seal 28 is secured across the lower end of the cartridge to prevent atmospheric contamination of the material M. A recessed area 29 is formed in the cartridge behind the seal to provide an area for receipt of the seal when it is ruptured by the male connector 50, to prevent interference with the liquid seal effected by the connector 50.

The cartridge and plunger are made from a suitable disposable material determined to be inert to the chemicals associated with peptide synthesis, such as Teflon, and, in a preferred embodiment, the cartridge body 20 will be injection molded from low-density polyethylene (LDPE), while the plunger 14 will be injection molded from polypropylene. The frit 25 is also manufactured from polypropylene and may be purchased from Porex Technologies, Stock No. X-5616. The seal 28 comprises a thermoplastic coated foil membrane and may be purchased from 3M and cut to size. The seal is applied to the cartridge body by induction heating using commercially available equipment (not shown or described).

Figure 6:
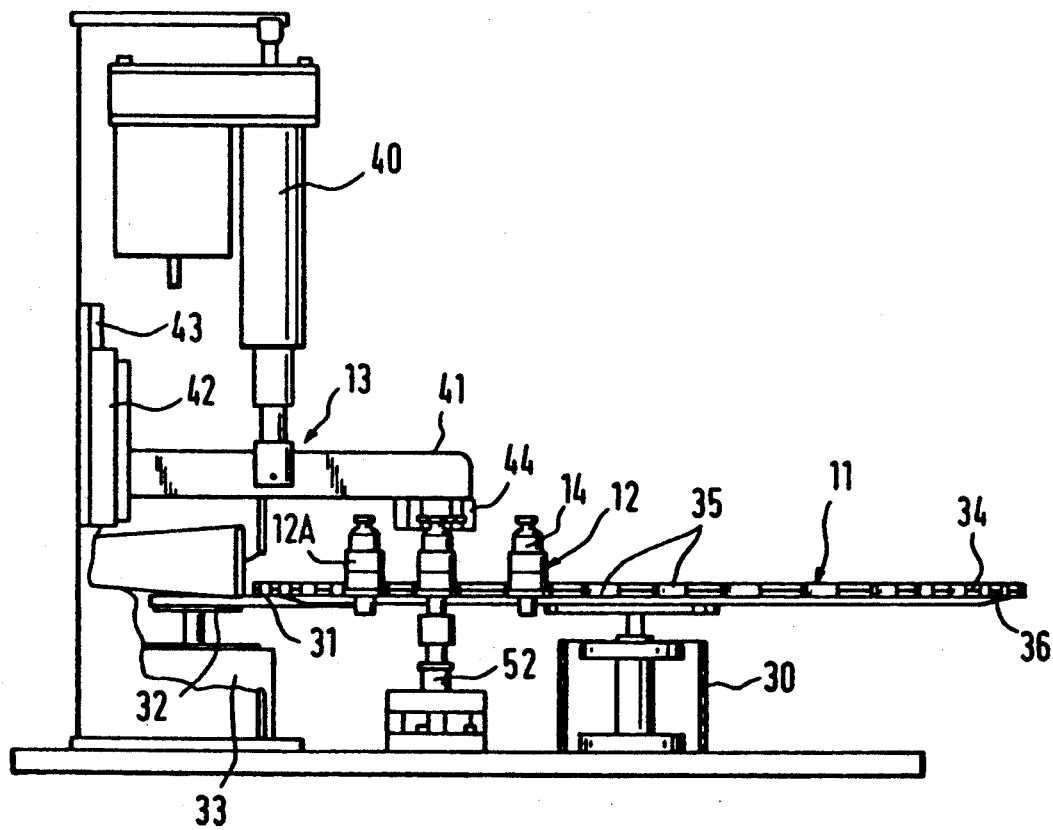
FIG. 6 is a side view in elevation, with portions broken away, of the carousel, gripper and fluid system connection used in the system of the invention.
Figure 7:
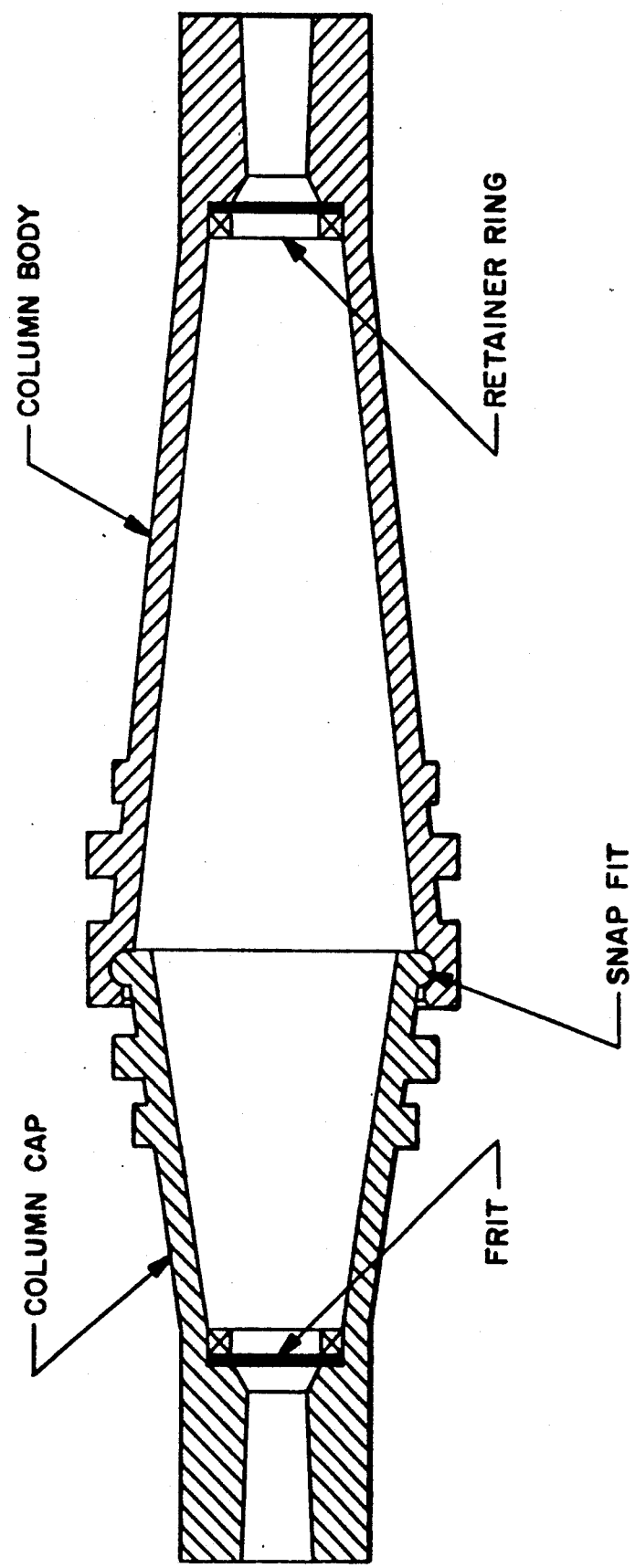
FIG. 7 is an enlarged longitudinal sectional view of the unique reactor column used in the invention.

The carousel 11 is removably supported on a bearing block 30 and is driven via belt 31 and pulley 32 by a motor 33. The carousel comprises a top plate 34 having a plurality of radial slots 35 in its peripheral edge, and a cartridge spring plate 36 engaged beneath the top plate. In use, the flange 24 on the cartridge 12 is engaged between the top plate 34 and spring plate 36, with the cartridge body extending through the slot 35 so that the lower end thereof with the female connector 23 is positioned below the spring plate and the upper end with the plunger 14 is positioned above the top plate (see FIGS. 1 and 6).

Suitable indicia 37 is provided on the bottom surface of the spring plate in a position to be detected by a position sensor $S_1$, which controls operation of the motor 33 and defines a "parked" or home position for the carousel. Another sensor $S_2$ detects the position of the most recent "spent" cartridge 12A.

In a preferred embodiment, a plurality of slots 35, preferably 40, will be provided in the carousel for holding forty cartridges. The cartridges in the embodiment described herein are hand loaded into the slots in a predetermined order depending upon the intended use for the apparatus. After the cartridges have been loaded into the carousel, the carousel is placed in the apparatus and "home" position determined by the location of the indicia 37 and sensor $S_1$. Alternatively, the carousel may be loaded when the carousel is in place on the bearing block 30.

The gripper mechanism 13 comprises a linear actuator 40 connected to an arm 41 midway between the ends of the arm. The arm has a slide 42 on one end riding on a track 43, and a plunger gripping slot 44 on its other end. Thus, operation of the actuator 40 causes the arm 41 to move up and down in a straight line or vertical path relative to the carousel and a cartridge 12 supported therein.

Upon initiation of a cycle of operation (via appropriate command given through the computer and the board 18) and loading of the carousel as described above, the gripper arm 41 is lowered in front of the next succeeding cartridge plunger flange 27 until the flange is directly in line with the gripper slot 44 on the arm 41. Optical or other suitable sensors detect and insure the precise location. The carousel is then advanced to engage the plunger flange 27 with the gripper slot 44.

The fluid connector 16 is positioned beneath the carousel in position to be in alignment with the lower end of a cartridge when the cartridge is positioned to engage the flange of its plunger with the gripper slot 44, as described above, and comprises a male connector 50 (see FIG. 2) having a tapered end 51 for piercing the foil seal 28 on the cartridge lower end and making a frictional engagement in the female recess. The male connector is mounted through a spring-loaded connection on a reciprocable member 52 operated by pneumatic motor 53 via valves $V_1$ and $V_2$ from unregulated supply line 54. The male connector 50 is connected with the fluid transport system 15 via a fluid line 55 extending between the connector and a valve $V_3$. A fluid sensor $S_F$ is associated with line 55 to detect the presence of fluid in the line. Thus, when the cartridge has been advanced and its plunger flange engaged with the gripper slot 44, the male connector is actuated to pierce the seal 28 and establish fluid communication between the contents of the cartridge and the fluid system.

After connection of the cartridge to the fluid transport system, the gripper mechanism is raised, thereby raising the plunger and drawing solvent and reagent into the cartridge to be admixed with the amino acid mixture. Several different reservoirs $R_1$, $R_2$, $R_3$, $R_4$, $R_5$ and $R_6$ are provided, for containing one or more reagents. Each reservoir has a three-port, two-way valve connected with it, as at $VR_1$, $VR_2$, $VR_3$, $VR_4$ and $VR_5$, respectively. In addition, one of the reservoirs, $R_6$, comprises an external, four liter bottle and there are three three-port, two-way valves $VR_6A$, $VR_6B$ and 74 connected with it. As seen in FIG. 1, the valves $VR_1$, $VR_2$, $VR_3$, $VR_4$ and $VR_5$ are arranged in two banks $B_1$ and $B_2$ associated with the reservoirs $R_1$ and $R_2$, and with $R_3$, $R_4$ and $R_5$, respectively. External reservoir $R_6$ is connected via its valves to each of the banks.

A further three-port, two-way valve 60 is connected in a fluid conduit 61 extending between the two banks of valves, and two two-port valves 62 and 63 are interposed in this conduit between the valve 60 and each bank of valves.

A waste conduit 64 leads from the valve 60 to a suitable waste disposal site, and a two-port valve 65 is interposed in this conduit. A fluid sensor $S_F$ is associated with this waste conduit to detect the presence of fluid in the conduit.

Fluid conduit 61 and bank $B_2$ are connected to different ports of a three-port, two-way valve 70, which is, in turn, connected to the lower end of reactor column 17. A fluid sensor $S_F$ is associated with the conduit 71 leading from the valve 70 to the reactor column 17.

The upper end of the reactor column is connected via conduit 72 to series-connected three-port, two-way valves 73 and 74 and two-port valve 75. An outlet conduit 76 leads from valve 73 to waste, and a conduit 77 connects valve 74 with the reservoir $R_6$. Valve 75 is connected via conduit 78 with a first manifold 79 for distributing pneumatic pressure to the system.

Manifold 79 is also connected via conduit 80 and two-port valve 81 with the first bank $B_1$ of valves, and via conduit 82 and two-way, two-position valve 83 to the bank $B_2$ of valves.

A second manifold 90 for distributing pneumatic pressure is connected via conduits 91, 92, 93, 94, 95 and 96 wit the respective reservoirs for pressurizing the contents of the reservoirs to assist in the movement of fluids through the system. Venting of all reservoirs is provided by a manual toggle 103. The line 93 to the piperidine deblock reservoir $R_3$ is also equipped with a non-return check valve 106 to prevent contamination of other solvents and reagents by piperidine vapor.

The first manifold 79 is provided with regulated pressurized gas via conduit 100 and pressure regulator 101, while the second manifold 90 is provided with regulated pressurized gas via conduit 102, regulator 101 and three-port, three-way valve 103 operated either manually or by pressure switch 104.

Gas to the system is through flow meter 105 and, in a preferred embodiment, is at 30 psi, regulated to about 6 psi. Additionally, the gas is inert with respect to the various chemicals used in the process.

The valves are solenoid controlled, and with the fluid sensors and motor controls $MC_1$ and $MC_2$ are connected with controller 110, which is responsive to commands from the board 18 and computer (not shown). A communication port 111 is provided on the board for connection to the computer, and a suitable power supply 112 is also connected to the board.

The fluid conduits, valve components, manifolds, reservoirs and other components coming into contact with the fluids being handled by the system are made from a material inert to the fluids, such as Teflon, polypropylene, polyethylene and stainless steel. The gas used to provide pneumatic pressure in the system will be an inert gas, such as nitrogen, argon or helium. Selection of the gas will be determined by its mixing characteristics within the reactor column. Further, the cartridges may be provided with a bar code and a suitable reader 113 positioned to sense the bar code for confirmation of proper cartridge position and sequence.

The reagent reservoirs, valves and electronics are supported in a sheet metal housing. The electronics and pneumatics may be housed in a tray assembly that can be removed from the rear of the housing; and the carousel, gripper assembly and fluid connection structure comprise a single, replaceable assembly. A large door in the front of the housing permits access to the five fixed position reagent bottles. Most of the valves and the pneumatics are also accessible through doors in the rear of the housing.

Alongside the housing are three one gallon bottles: one for DMF and the other two for waste. Special vapor traps containing Dowex 50W-X8 ion exchange resin (sulfonic acid) allow the waste bottles to be vented directly into the laboratory.

In a typical setup for peptide synthesis, each cartridge will contain 0.5 mmol of Fmoc amino acid, HOBt and BOP. The plunger will be inserted halfway into the cartridge, defining a volume of 2.5 ml in which the dry mixture is stored. The three component amino acid mixture is activated by withdrawing the plunger, drawing activator into the cartridge. The amino acid is dissolved and activated simultaneously. It is then expelled from the syringe on the downward stroke of the plunger and directed into the reactor column. The porous frit in the bottom of the cartridge acts to prevent insoluble residues or reaction by-products from entering reaction and valving systems. By reciprocating the plunger, the amino acid solution, as well as up to 5 ml of other synthesis reagents may be continuously moved through the reactor column. The reciprocation further aids in the mechanical dissolution of poorly soluble materials.

The cartridges are designed to last for 200 pumping cycles. Each spent cartridge is replaced at the end of the coupling cycle by a fresh cartridge containing the next amino acid in the sequence.

To disengage the cartridge plunger, all fluid is first expelled from the cartridge. The fluid supply lines are then disconnected and the carousel is advanced until the gripper is clear of the plunger. The gripper is then fully raised and the carousel advanced to bring the next cartridge into operative position for engagement with the gripper, and the operation as described above repeated.

In a typical operation involving peptide synthesis, there are only two distinct procedures within the Fmoc coupling cycle: deblock and couple, separated by an efficient DMF wash, see, e.g., co-pending Hudson application Ser. No. 044,185, filed Apr. 30, 1987, and Melenhofer, U.S. Pat. No. 4,108,846, issued Aug. 22, 1978, and entitled "SOLID PHASE SYNTHESIS WITH BASE N ALPHA-PROTECTING GROUP CLEAVAGE", both of which are incorporated herein by reference in their entirety. Synthesis is carried out on either Pepsyn K or polystyrene solid supports. Initial deblock of the resin is achieved with 30% piperidine in DMF for 10 minutes, followed by 6-10 washes with DMF. The cycle is then begun by activating and coupling the amino acid as follows: 0.5 mmol of the Fmoc-amino acid, BOP and HOBt mixture is dissolved in 2.5 ml of activator and coupled to 0.1 mmol of support. Reaction times of 20 and 40 minutes are used, with continual reciprocation of the reaction mixture achieving uniform and efficient reaction. Subsequent to coupling, washing of the reactor is performed with DMF, and the cartridge is deblocked with 30% piperidine in DMF for 10 minutes, followed by 6-10 washes with DMF to end the cycle. The cartridge is then disposed of and a new cartridge positioned to repeat the cycle.

The same apparatus can be used in DNA synthesis, with 50-100 micromoles of support. Amidite derivatives are placed in the cartridges and then dissolved and activated by the addition of tetrazole in acetonitrile. Since the amidites are stored as solids, the problem of decomposition is obviated. Large excesses, e.g., 20-50 fold, are currently used in DNA synthesizers. The efficient mixing, washing and lack of decomposition provided by the invention permits operation with only a five fold excess. Consequently, large amounts of DNA can be prepared rapidly and economically.

Typical control commands can be employed and other functions can be added or substituted in the foregoing system which alterations should be within the purview of one skilled in this art. In operation, typically, the following steps will be employed. Solid phase peptide synthesis with the Excell involves the following steps:

1. Insert sequence commands to computer control.
2. Place support material in the column reactor.
3. Load cartridges and verify correctness with bar-code reader.
4. Load reagents and solvents.
5. Start up synthesis consisting of priming lines and washing reactor column.
6. Fmoc-removal. A blank cartridge measures and mixes piperidine with DMF. The removal reagent is reciprocated between the reactor and the syringe. After 3 minutes, this reagent is replaced with freshly diluted solution and removal contained for another 7 minutes.
7. Syringe is washed and dispensed with.
8. Column is washed (by bi-directional flow) to remove all piperidine.
9. All lines blown dry with argon.
10. Activator solution admitted to next cartridge containing the Fmoc-amino acid, BOP and HOBt. This effects complete dissolution, rapidly converts the amino acid into a form which will couple, and is transferred to the reactor and reciprocated to achieve uniform and complete reaction.
11. After coupling, excess amino acids are washed out of the system.

This completes one cycle of addition, this process is continued until the desired sequence is assembled, then the support is removed and the peptide obtained by mild acid cleavage.

The following is a specific description of operation of the embodiment described for peptide synthesis. The processes described, including priming, washing, deblocking, purging and coupling are general for any synthesis application. Flow and control for other applications may be varied to suit a specific synthesis operation.

1. User sequence selection or entry.
2. Set up. The proper reagents and solvents are placed in the reservoirs according to amounts calculated by the controller. The amino acid cartridges are then placed in the carousel in the correct sequent to be assembled. A blank cartridge is placed in the first position. Loading can be prompted by a display on the computer controller. The carousel next rotates the cartridges past the bar-code reader before any operation of the machine to VERIFY that loading has been performed correctly. Unnatural acids, D-amino acids, and user specific amino acids can be accommodated by the bar-code system used. Operation in the absence of verification is also possible.

3. Start up. Upon commencing operation, all opening the valve and waste (e.g., Act 1 is primed by operating $VR_7$, $VR_1$, 65, 60, and 62 for 4 seconds). All priming routines by-pass the column.

4. Valve train wash. DMF is washed through the activator and reagent valve trains to remove contamination ($VR_7$, $VR_6A$, 65, 60, 62) followed by ($VR_8$, $VR_6/B$, 63, 65 and 60).

5. The column and its contents, the synthesis support, are next thoroughly washed. This process consist of: i) upward washing (opening valves 73, $VR_8$, $VR_6/B$, 70); ii) a pause (8 seconds); iii) downward washing through column 17 (74, 70, 63, 65, 60); and iv) emptying of column 17 (75, 70, 63, 65, 60) by argon. Steps i) to iv) are then repeated once.

iv) The lines and column are then purged of all fluid with argon.

6. Deblock reagent dilution. The gripper 13 engages the first EMPTY cartridge, completely depressed the plunger, and then partially raises the plunger to admit 3 parts of piperidine ($VR_8$, $VR_3$, $VR_9$, 63, 62, $V_3$), the plunger is further raised to admit 7 parts of DMF ($VR_8$, $VR_6/B$, 63, 62, $V_3$).

7. Column deblocking, first treatment. The plunger is depressed delivering entire contents to column reactor (73, 70, 63, 62, $V_3$). After a pause (8 seconds), the deblocking mixture is drawn back into the syringe, then re-expelled. This process is continued for 3 minutes.

8. Column deblocking, second treatment. the contents of the syringe are dispelled to waste (plunger down, $V_3$, 62, 60, 65). The processes described in 6 and 7 above are then repeated to dilute further piperidine to 30% and perform deblocking for a second period of seven minutes.

9. Syringe emptying and line purging with argon to displace most piperidine. Syringe then filled with DMF ($VR_7$, $VR_6A$, $V_3$) and left.

10. Column is washed 6 times with DMF as described in Section 5, i)-iv).

11. Syringe emptied to waste. Then filled with DMF through the column (74, 70, 63, 62, $V_3$) and emptied to waste ($V_3$, 62, 60, 65). Repeated 4 times.

12. All lines and column are purged of fluid.

13. Gripper 13 disengages from spent cartridge. New cartridge is placed in position by advancing carousel 45 and gripping plunger.

14. Plunger is depressed ($V_3$, 62, 60, 65). Then withdrawn to admit 2.5 ml activator (0.3M N-methylmorpholine in DMF)($VR_1$, $VR_7$, $V_3$).

15. Coupling is performed by expelling activated amino acid to column (73, 70, 63, 62, $V_3$), then reciprocating fluid to ensure mixing, uniform reaction and complete amino acid dissolution. The withdrawal step involves activation of valves 75, 70, 63, 62 and $V_3$.

16. After adopted coupling time, the spent amino acid solution is displaced to waste. The cartridge is filled with DMF ($VR_7$, $VR_6A$, $V_3$) and left whilst the column is washed as in 5, i)-iv). Cartridge washing, as in 11, is then performed.

17. Fluid purging from system with argon.

18. Steps 6 and 7 are then repeated to assemble the desired sequence.

19. Final Fmoc group may be left on or removed.

20. Synthesis ends with methanol and methylene chloride washed and nitrogen purge through column.

21. Support removed from column and cleaved.

The foregoing system, system components, controls and method of operation are exemplary only and different synthesis, and equivalent apparatus, may be substituted for that disclosed, where appropriate, and still achieve the overall improvements taught herein. The scope of the invention is only limited by the claims and the applicable prior art.

We claim:

1. A system for automated chemical processing, comprising:

a plurality of chemical storage cartridges, at least one cartridge for storing a first chemical;

means for choosing between any one of said cartridges and holding said chosen cartridge and positioning said cartridge at a fixed location within said system;

a reservoir spaced from said location for containing a second chemical to be reacted with said first chemical in said chosen cartridge to produce a third chemical;

means at said location for fluid coupling to said chosen cartridge to establish fluid communication with the contents thereof;

a fluid conduit connected to said fluid coupling means and said reservoir to dissolve and conduct said first chemical from said chosen cartridge to said reservoir to react with said second chemical;

valve means operably connected with said fluid conduit for controlling flow through said conduit;

said cartridges including pump means operable when said chosen cartridge is positioned at said location for changing the internal volume thereof so as to cause bi-directional flow of said first chemical through said fluid coupling means, alternatively into and out of said reservoir and said chosen cartridge to promote mixing and reacting with said second chemical in said reservoir to complete the formation of said third chemical, said pump means comprises a plunger slidably sealed in said cartridges and a reciprocating arm connected with said plunger to reciprocate said plunger when said chosen cartridge is at said location to alternately draw material into said chosen cartridge and then expel the material from said chosen cartridge; and automatically operated control means connected with said pump means and said valve means to obtain a predetermined sequence of operation of said pump means and said valve means for controlling the dispensing of said first and second chemicals and the further processing of said third chemical.

2. A system as claimed in claim 1, wherein:

said cartridges include a diametrically enlarged flange formed on the outside of the body thereof between the ends thereof for attachment of said cartridges to a support apparatus.

3. A system as claimed in claim 2, wherein:

a porous member is secured in said body adjacent to and covering lower end thereof to define a mechanical barrier to leakage of chemical from the interior of said cartridges.

4. A system as claimed in claim 1, wherein:

a source of pneumatic pressure is connected with said reservoir to pressurize the contents thereof and to assist in flow of said first chemical into and out of said reservoir.

5. A system as claimed in claim 4, wherein:

said system comprises a protein synthesis apparatus, and said reservoir includes a reactor column connected in series with said fluid conduit for receiving said first chemical from said chosen cartridge.

6. A system as claimed in claim 5, wherein:

said automatically operated control means includes a computer programmed to operate said valve means and said pump means in said predetermined sequence.

7. A system as claimed in claim 5, wherein:

said reactor column for holding said solid supports comprises a molded body of material inert to chemicals being handled in said column, said body including an elongate inlet portion having opposite open ends, and an elongate outlet portion having opposite open ends, said inlet and outlet portions being releasably snap-fitted together at one of their ends in coaxial relationship with one another, a block of porous material secured in the other end of each of the inlet and outlet portions to provide a mechanical barrier to leakage of solid material from the column, and means on each of the other ends of the inlet and outlet portions for connection of said column to a fluid delivery system.

8. A system as claimed in claim 1, wherein:

said cartridge choosing means comprises a rotating carousel having means for holding and supporting said cartridges thereon; and said control means is connected to operate said carousel in timed sequence with operation of said valve means and said pump means.

9. A system as claimed in claim 8, wherein:

said rotatable carousel for holding and advancing said cartridges having an exterior flange thereon, said carousel further comprising:
- a top plate having a peripheral edge with a plurality of radially extending slots therein; and
- a bottom plate secured beneath the top plate to clamp between the top and bottom plates the flange of one of said cartridges received in a slot in the top plate, whereby said one cartridge is supported in an upright position by said carousel.

10. A system as claimed in claim 9, wherein:

said bottom plate comprises a spring plate resiliently and yieldably biased against the underside of said top plate.

11. A system as claimed in claim 8, wherein:

said fluid coupling means includes means movable into and out of contact with said chosen cartridge at said location; and said control means is connected to operate said fluid coupling means in timed sequence with operation of said carousel, said pump means and said valve means.

12. A system as claimed in claim 11, wherein:

sensors are positioned adjacent said carousel, said pump means and said fluid coupling means to detect the position and status thereof and in response thereto to send a signal to said control means to insure operation of said carousel, pump means and fluid coupling means in proper timed sequence.

13. A system as claimed in claim 12, wherein:

said carousel comprises a disc-shaped member having a plurality of slots in a peripheral edge thereof, said cartridges being supported in each of said slots.

* * * * *